(12) United States Patent
Single et al.

(10) Patent No.: US 11,129,980 B2
(45) Date of Patent: Sep. 28, 2021

(54) ELECTRODE ASSEMBLY

(71) Applicant: Saluda Medical Pty Limited, Artarmon (AU)

(72) Inventors: Peter Scott Vallack Single, Artarmon (AU); Jonathan Brereton Scott, Artarmon (AU); Steven Owen McCabe, Artarmon (AU); John Louis Parker, Artarmon (AU)

(73) Assignee: Saluda Medical Pty Limited, Artarmon (AU)

( * ) Notice: Subject to any disclaimer, the term of this patent is extended or adjusted under 35 U.S.C. 154(b) by 59 days.

(21) Appl. No.: 16/489,908

(22) PCT Filed: Mar. 2, 2018

(86) PCT No.: PCT/AU2018/050191
§ 371 (c)(1),
(2) Date: Aug. 29, 2019

(87) PCT Pub. No.: WO2018/157214
PCT Pub. Date: Sep. 7, 2018

(65) Prior Publication Data
US 2020/0001075 A1 Jan. 2, 2020

(30) Foreign Application Priority Data
Mar. 2, 2017 (AU) ................................ 2017900721

(51) Int. Cl.
A61B 5/00 (2006.01)
A61N 1/08 (2006.01)
(Continued)

(52) U.S. Cl.
CPC ............ A61N 1/086 (2017.08); A61B 5/6868 (2013.01); A61B 18/14 (2013.01); A61N 1/0529 (2013.01);
(Continued)

(58) Field of Classification Search
CPC ........ A61B 2017/00004; A61B 5/6868; A61N 1/0529; A61N 1/0551; A61N 1/086; H01R 2201/12
See application file for complete search history.

(56) References Cited

U.S. PATENT DOCUMENTS 5,782,645 A  7/1998 Stobie et al.
2005/0261754 A1* 11/2005 Woloszko ............ A61B 18/148
                                                              607/99
(Continued)

FOREIGN PATENT DOCUMENTS

WO  2008002654 A2  1/2008
WO  2010053585 A1  5/2010

OTHER PUBLICATIONS

EP; Extended European Search Report in the Application No. 18760681.9 dated Nov. 20, 2020.
(Continued)

Primary Examiner — George Manuel
(74) Attorney, Agent, or Firm — Snell & Wilmer L.L.P.

(57) ABSTRACT

An electrode assembly (1) for an active implantable medical device comprising: an elongated, biocompatible, electrically non-conductive body (3) having a first portion (7) and a second portion (9); one or more biocompatible, electrically conductive filaments (5) inside the elongated non-conductive body (3) between the first portion (7) and the second portion (9); and one or more fluid passages (11) along the elongated electrically non-conductive body (3) between the first portion (7) and second portion (9), wherein the one or more fluid passages (11) allow a surrounding fluid (13) of a patient to be in electrical contact with the one or more conductive filaments (5). There is also disclosed a method of manufacturing an electrode assembly.

18 Claims, 16 Drawing Sheets

(51) Int. Cl.
  *A61B 18/14*    (2006.01)
  *A61N 1/05*    (2006.01)
  *A61B 17/00*    (2006.01)
(52) U.S. Cl.
  CPC .. *A61N 1/0551* (2013.01); *A61B 2017/00004* (2013.01); *H01R 2201/12* (2013.01)

(56) References Cited

U.S. PATENT DOCUMENTS

| | | |
|---|---|---|
| 2006/0200218 A1 | 9/2006 | Wahlstrand |
| 2006/0282146 A1 | 12/2006 | Aron et al. |
| 2009/0099441 A1 | 4/2009 | Giszter et al. |
| 2010/0262214 A1 | 10/2010 | Robinson |
| 2012/0277544 A1 | 11/2012 | Fernandes et al. |
| 2014/0324143 A1 | 10/2014 | Robinson et al. |
| 2015/0151107 A1 | 6/2015 | Schouenborg |
| 2016/0144189 A1 | 5/2016 | Bakker et al. |
| 2016/0023967 A1 | 8/2016 | Shan et al. |

OTHER PUBLICATIONS

Australian Patent Office, International Search Report and Written Opinion of the International Searching Authority, dated May 1, 2018, 12 pages.

\* cited by examiner

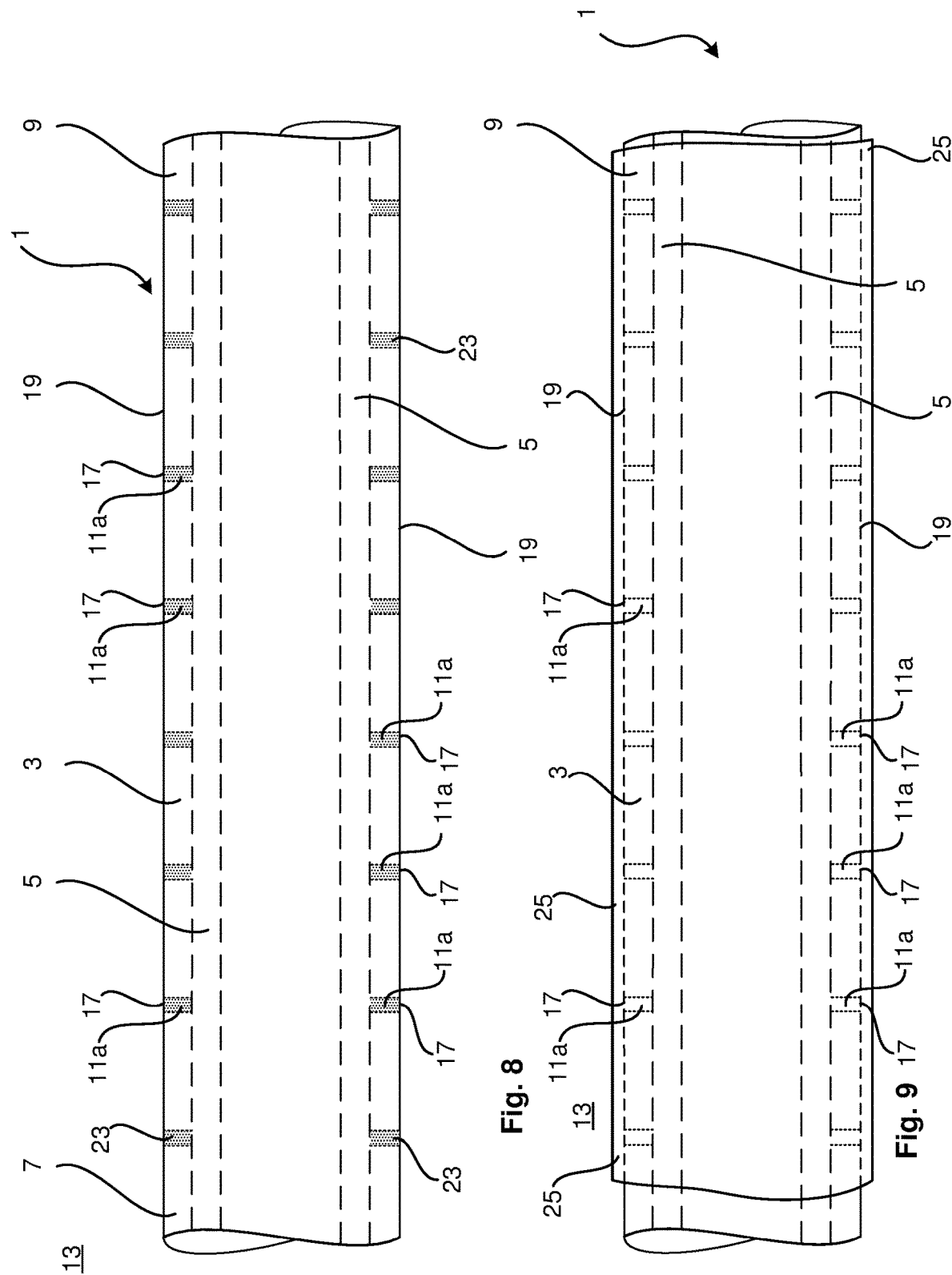

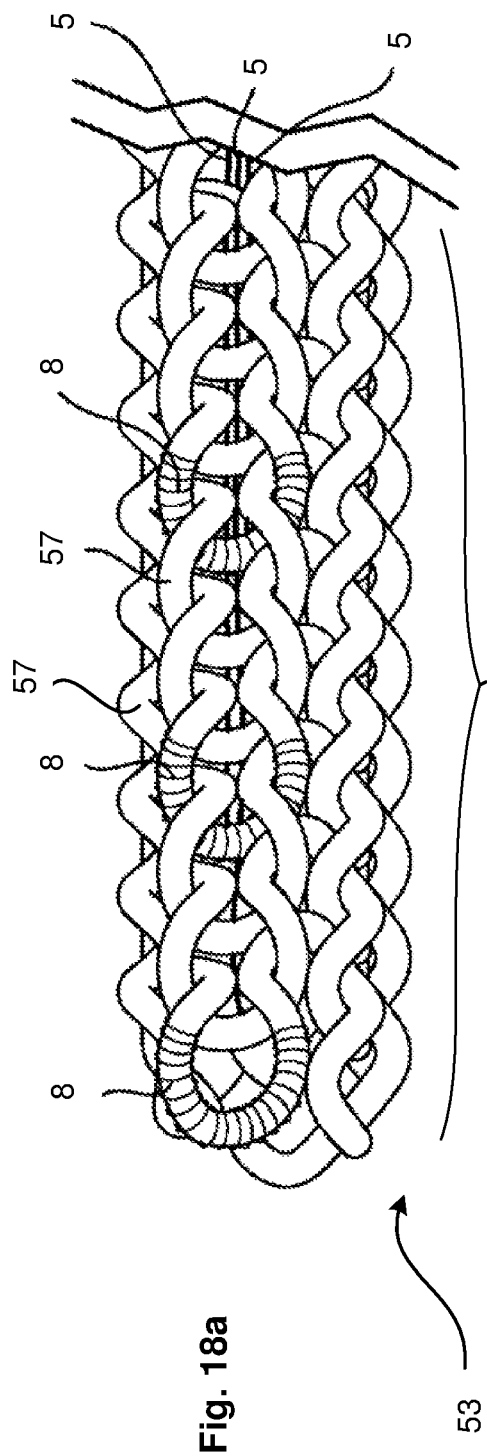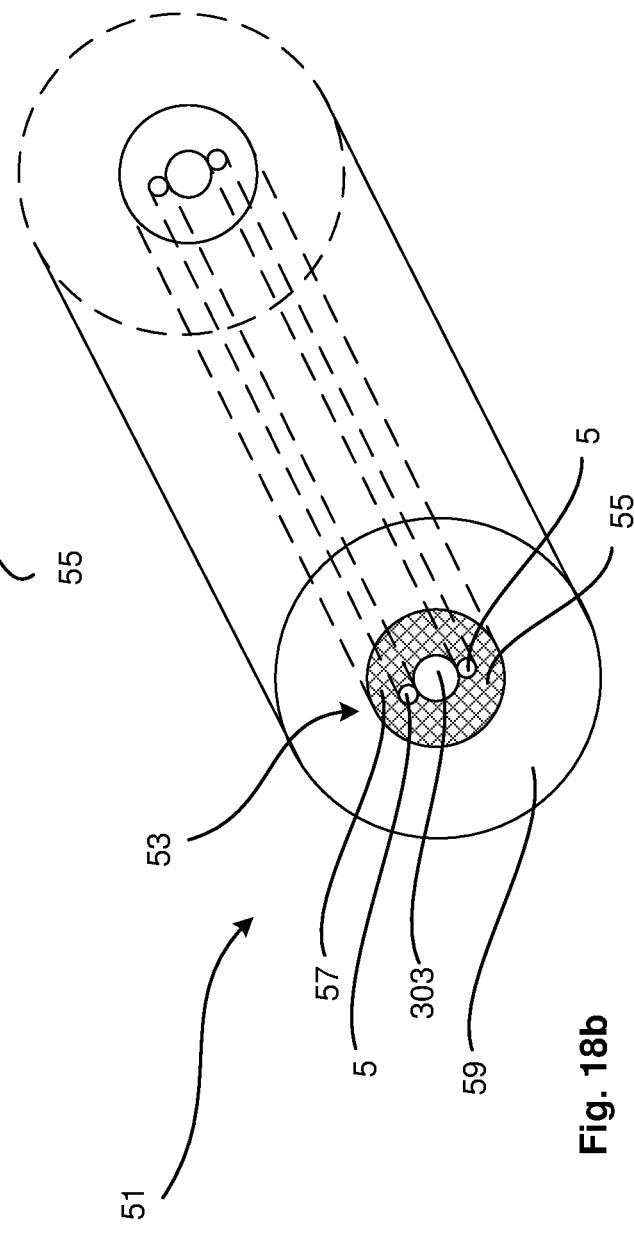
Fig. 18a
Fig. 18b

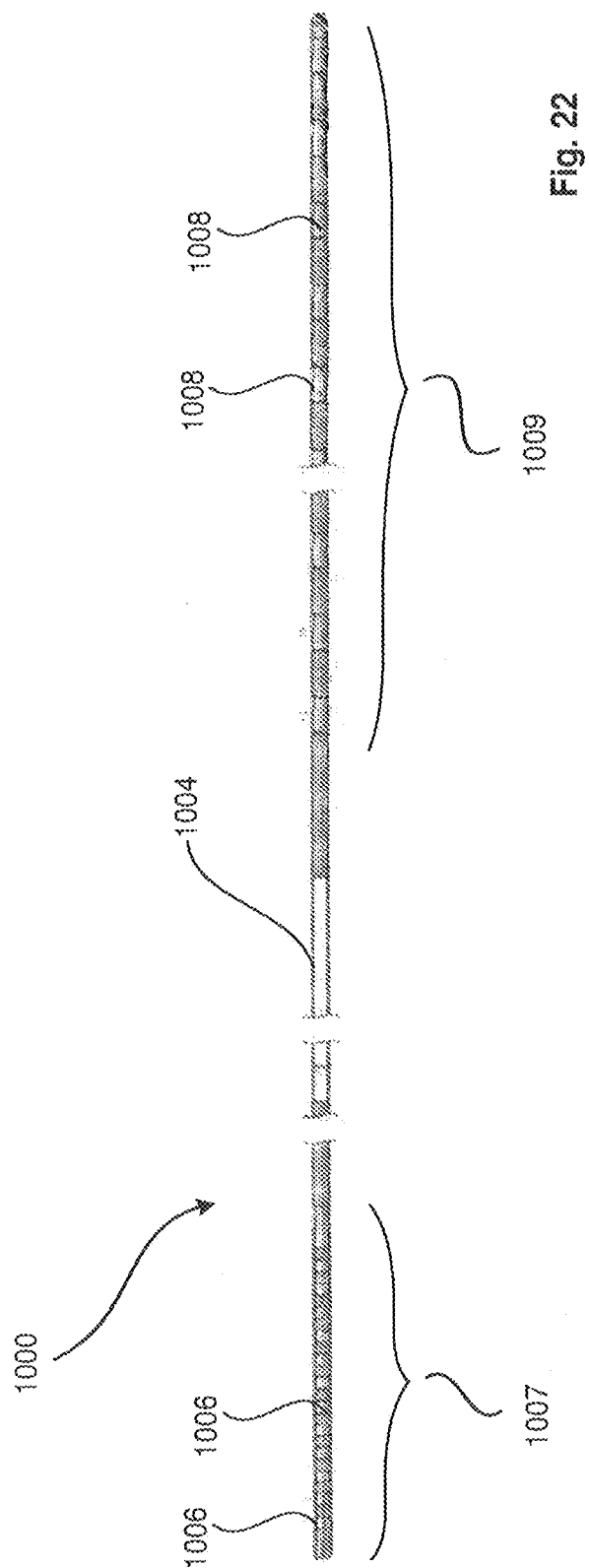
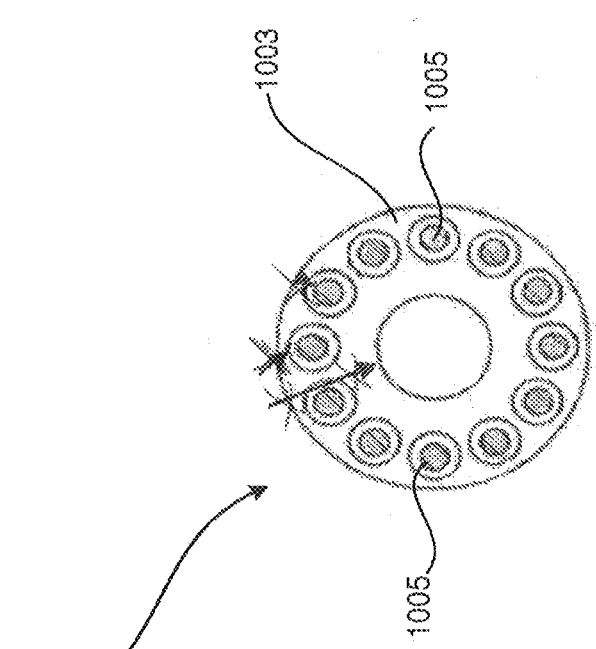

ELECTRODE ASSEMBLY

TECHNICAL FIELD

The present disclosure relates to an electrode assembly for an active implantable medical device (AIMD) for implanting into tissue of a patient.

BACKGROUND

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

In particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member, and are electrically connected to the electronics module. The electrodes and the non-conductive member are collectively referred to herein as an electrode assembly.

For neuro-stimulators, the tissue interface is a stimulating lead 1000 which delivers electrical pulse to a specific nerve or tissue. This lead 1000 may consist of a long thin non-conductive (and insulating) body 1004 and a number of conductive rings 1006, 1008 at both ends 1007, 1009 of the body 1004. Referring to FIGS. 22 and 23, the rings 1008 at a therapeutic end 1009 are known as electrodes and the rings 1006 at the connector end 1007 are known as contacts, where the electrodes are connected to the contacts along the long thin non-conductive body 1004. An example of the long thin non-conductive body 1004 is shown in the cross-section in FIG. 23 that shows conductive wires 1005 surrounded by a non-conductive body 1003.

Patients with an implanted neuro-stimulator and associated lead may have issues undergoing magnetic resonance imaging (MRI). The MRI uses three types of fields to create an image: a static magnetic field; a radiofrequency (RF) magnetic field; and a gradient magnetic field. Exposure to these fields may cause heating to the leads. This heating may result in tissue burns and damage (which may not be immediately felt by the patient). Another potentially damaging effect is damage to the implant due to radiofrequency energy being transmitted from the lead. This can lead to reprogramming, damage to the implant or explant of the implant. Additionally, the MRI could cause a temporary unintended stimulation due to induced voltage through the assembly and system.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

There have been attempts to provide designs for MRI safe leads. US patent publication U.S. Pat. No. 8,798,767 B2 illustrates a method of reducing the heat caused by MRI conditions. This document suggests coiling conductors in a multi-layer structure, with each coil layer electrically connected to the next to provide parallel conductive paths. However, this method may result in high inductance when exposed to MRI radiation. US patent publication U.S. Pat. No. 9,050,457 B2 uses a similar approach with a lead body and multi-layer coil conductor within the length of the lead body. The stiffness of the multi-layer coil conductor is similar to the lead body, ensuring consistent mechanical properties of the lead. US patent publication U.S. Pat. No. 9,302,101 B2 uses a different approach with the lead body providing an additional path for containing conductive material. This path spans at least a section of the length of the lead for conducting the induced RF energy away from the conductive wire of the lead.

In light of the above mentioned issues, it would be advantageous to have an electrode assembly, such as one used in an implantable medical device, that may be implanted in a patient whilst the patient is undergoing magnetic resonance imaging. This may include providing an implantable electrode assembly which, when exposed to an MRI environment, does not generate significant heat in the leads due to electromagnetic currents. In may be further advantageous for an implantable medical device that can operate during magnetic resonance imaging without, or with reduced, side effects described above.

An electrode assembly for an active-implantable medical device comprising: an elongated, biocompatible, electrically non-conductive body having a first portion and a second portion; one or more biocompatible, electrically conductive filaments inside the elongated non-conductive body between the first portion and the second portion; and one or more fluid passages along the elongated electrically non-conductive body between the first portion and second portion. The one or more fluid passages allow a surrounding fluid of a patient to be in electrical contact with the one or more conductive filaments.

When implanted in the tissue of a patient, the surrounding fluid of a patient is in electrical contact with the electrically conductive filaments. This fluid, such as saline, is electrically conductive and therefore reduces (or eliminates) the high capacitive coupling due to exposure of electromagnetic fields in the MRI environment. In particular, the RF frequency that induces an alternating current at a surface of the electrically conductive filaments will be electrically shorted by the fluid. On the other hand, lower frequency or direct current used for stimulation (i.e. when used with the AIMD), will take the lowest resistance such as at the core of the electrically conductive filaments (in contrast with the through the surrounding fluid).

Therefore the electrode assembly, when implanted in a patient, may allow the patient to undergo MRI without, or with reduced, adverse effects as noted above. In some examples, the electrically conductive filaments may have a very thin insulating coating that is in contact with the surrounding fluid.

The electrode assembly may further comprise a plurality of apertures along the elongated electrically non-conductive body, wherein the plurality of apertures provide the fluid passages from an outer surface of the electrically non-conductive body to the one or more conductive filaments.

The electrode assembly may also comprise one or more conductive filament lumens to receive respective conductive filaments passing though the elongated electrically non-conductive body, wherein the one or more conductive filament lumens has a diameter greater than the respective conductive filament lumens to provide at least part of the one or fluid passages.

The electrode assembly may further comprise one or more channels along the elongated electrically non-conductive body, wherein the one or more channels provide the one or more fluid passages from an outer surface of the electrically non-conductive body to the one or more conductive filaments.

In the electrode assembly, the elongated electrically non-conductive body may comprise a biocompatible non-biodegradable polymer.

The electrode assembly may further comprise one or more plugs in the one or more fluid passages, wherein the plugs comprise a biocompatible biodegradable material and wherein the one or more plugs biodegrade in a body of the patient after implantation.

The electrode assembly may further comprise a biocompatible biodegradable sheath to surround the elongated electrically non-conductive body, wherein the biodegradable sheath biodegrades in a body of the patient after implantation.

In the electrode assembly, the biocompatible biodegradable material may include polyvinyl alcohol.

The electrode assembly may further comprise a central lumen 35 in the elongated electrically non-conductive body to receive a stylet. In the electrode assembly, the biocompatible, elongated electrically non-conductive body may comprise: an outer wall; and a cavity within the outer wall, the cavity containing the one or more conductive filaments disposed within a biocompatible biodegradable material, wherein the biodegradable material biodegrades in a body of a patient after implantation.

The electrode assembly may further comprise a core disposed in the cavity, wherein the one or more filaments are helically disposed around the core.

The electrode assembly may further comprise a biocompatible, electrically non-conductive and needle-piercable base, wherein the elongated electrically non-conductive body, having the one or more conductive filaments, is stitched to the needle-piercable base.

In the electrode assembly, the elongated electrically non-conductive body may be stitched to the needle-piercable base with a biocompatible, electrically non-conductive filament sewn into the base.

An electrode assembly for an active implantable medical device comprising: a biocompatible porous support body; and one or more biocompatible electrically conductive filaments inside the porous support body from a first portion to a second portion, wherein the porous support body provide fluid passages to allow a surrounding fluid of a patient to be in electrical contact with the one or more conductive filaments.

The electrode assembly may further comprise a core disposed in the porous support body, wherein the one or more filaments are helically disposed around the core.

In the electrode assembly, the core may include a central lumen to receive a stylet.

In the electrode assembly, the at least one or more conductive filaments may comprise a plurality of the conductive filaments arranged in a matrix in the porous support body.

In the electrode assembly, the plurality of conductive filaments may be substantially parallel to one another in the matrix to prevent the conductive filaments from directly contacting one another.

An electrode assembly for an active implantable medical device, the electrode assembly comprising a textile assembly, having a textile structure. The textile assembly comprises: one or more biocompatible, electrically non-conductive filaments; and one or more biocompatible, electrically conductive filaments. The electrode assembly also comprises a bio-compatible, electrically non-conductive and non-woven base that surrounds at least one section of the textile assembly. The textile structure is porous to allow a surrounding fluid of the patient to be in electrical contact with the one or more conductive filaments.

In the electrode assembly, the textile assembly may be a knitted assembly, and the textile structure is an intermeshed loop structure.

In the electrode assembly, the textile assembly may be a braided assembly and the textile structure is a braided structure comprising braiding of the one or more non-conductive filaments and the one or more conductive filaments.

In the electrode assembly, the base may be applied to surround the textile assembly by electro spinning.

The implanted electrode assembly may be coupled with the active implantable medical device and in contact with the surrounding fluid so that it has a capacitance in the range of 0.25 nanofarads to 3.30 nanofarads per metre.

The capacitance per unit length of the lead depends on the permittivity and the thickness of the non-conductive body (which acts as an insulator). A capacitor is formed between the conductive filament and the surrounding tissue to form an impediment to current flow between the conductive filament and the tissue. Therefore it is desirable to have the capacitance to be high enough so that the current is not impeded. The capacitance value increases with higher filament diameter and higher permittivity of the non-conductive body. Furthermore, the capacitance value decreases with decreasing thickness of the non-conductive body.

A method of manufacturing an electrode assembly for an active implantable medical device, comprising:

providing an elongated biocompatible, electrically non-conductive body;

locating one or more biocompatible, electrically conductive filaments though the elongated non-conductive body from a first portion to a second portion; and forming one or more fluid passages along the elongated electrically non-conductive body between the first portion and the second portion, wherein the one or more fluid passages allow a surrounding fluid of a patient to be in contact with the one or more conductive filaments.

The method of manufacturing an electrode assembly, wherein the method may further comprise forming a plurality of apertures along the elongated electrically non-conductive body to provide the fluid passages from an outer surface of the electrically non-conductive body to the one or more conductive filaments.

The method of manufacturing an electrode assembly, wherein the method may further comprise forming one or more conductive filament lumens inside the elongated electrically non-conductive body to receive respective electrically conductive filaments, wherein the one or more conductive filament lumens has a diameter greater than the respective conductive filament lumens to form at least part of the one or fluid passages.

The method of manufacturing an electrode assembly, wherein the method may further comprise forming one or more channels along the elongated electrically non-conductive body, wherein the one or more channels provide the one or more fluid passages from an outer surface of the electrically non-conductive body to the one or more conductive filaments.

The method of manufacturing an electrode assembly, wherein the method may further comprise filling one or more fluid passages with one or more plugs, wherein the plugs comprise a biocompatible biodegradable material, wherein the one or more plugs biodegrade in a body of the patient after implantation.

The method of manufacturing an electrode assembly, wherein the method may further comprise surrounding the elongated biocompatible, electrically non-conductive body with a biocompatible biodegradable sheath, wherein the biodegradable sheath biodegrades in a body of the patient after implantation.

The method of manufacturing an electrode assembly, wherein the method may further comprise forming a central lumen in the elongated electrically non-conductive body, wherein the central lumen is configured to receive a stylet.

In the method of manufacturing an electrode assembly, the elongated electrically non-conductive body may comprise an outer wall that defines a cavity within, and the method may further comprise surrounding the one or more conductive filaments with a biodegradable material, wherein the biodegradable material and conductive filaments are provided inside a cavity, and wherein the biodegradable material biodegrades in a body of a patient after implantation.

The method of manufacturing an electrode assembly may further comprise helically disposing the one or more conductive filaments around a core.

The method of manufacturing an electrode assembly may further comprise stitching the elongated, biocompatible, electrically non-conductive body to a biocompatible, electrically non-conductive and needle-piercable base.

A method of manufacturing an electrode assembly for an active implantable medical device, comprising:
providing one or more biocompatible, electrically conductive filaments; and
forming a biocompatible, porous support body around the one or more biocompatible electrically conductive filaments;
wherein the porous support body provide fluid passages to allow a surrounding fluid of a patient to be in electrical contact with the one or more conductive filaments.

The method of manufacturing an electrode assembly may further comprise: providing a core; and helically disposing the one or more conductive filaments around the core.

The method of manufacturing an electrode assembly may further comprise forming a central lumen in the core.

In the method of manufacturing an electrode assembly, the one or more biocompatible electrically conductive filaments may comprise a plurality of conductive filaments, and the method may further comprise arranging the plurality of conductive filaments in a matrix in the porous support body.

A method of manufacturing an electrode assembly for an active implantable medical device, comprising:
providing a textile assembly, having a textile structure, comprising:
one or more biocompatible, electrically non-conductive filaments; and
one or more biocompatible, electrically conductive filaments; and
surrounding at least one section of the textile assembly with a biocompatible, electrically non-conductive and nonwoven base,
wherein the textile structure is porous to allow a surrounding fluid of the patient to be in electrical contact with the one or more conductive filaments.

In the method of manufacturing an electrode assembly, the textile assembly may be a knitted assembly, and the textile structure is an intermeshed loop structure, and wherein the step of providing a textile assembly comprises knitting the one or more non-conductive filaments with the one or more conductive filaments.

In the method of manufacturing an electrode assembly, wherein the textile assembly may be a braided assembly and the textile structure is a braided structure, and wherein the step of providing a textile assembly comprises braiding the one or more non-conductive filaments with the one or more conductive filaments.

In the method of manufacturing an electrode assembly, surrounding the at least one section of the textile assembly with a biocompatible electrically non-conductive and nonwoven base may comprise applying the base by electrospinning.

An electrode assembly for an active implantable medical device comprising: an elongated, biocompatible, electrically non-conductive body having a first portion and a second portion; one or more biocompatible, electrically conductive filaments inside the elongated non-conductive body between the first portion and the second portion; wherein the electrode assembly is configured to be coupled with the active implantable medical device and in contact with the surrounding fluid to have a capacitance in the range of 0.25 nanofarads to 3.30 nanofarads per metre.

A method of manufacturing an electrode assembly for an active implantable medical device, comprising: providing an elongated biocompatible, electrically non-conductive body; locating one or more biocompatible, electrically conductive filaments though the elongated non-conductive body from a first portion to a second portion; and coupling the electrode assembly with the active implantable medical device and locating the electrode assembly to be in contact with the surrounding fluid to have a capacitance in the range of 0.25 nanofarads to 3.3 nanofarads per metre.

BRIEF DESCRIPTION OF DRAWINGS

FIG. 8 illustrates another example of an electrode assembly for an active implantable medical device having biodegradable plugs;

FIG. 9 illustrates another example of an electrode assembly for an active implantable medical device having a biodegradable sheath;

FIGS. 18a and 18b illustrates another example of an electrode assembly for an active implantable medical device having a textile assembly that includes a knitted assembly;

FIG. 22 is a side view of an example of an electrode assembly for an active implantable medical device including a connector end and a therapeutic end; and FIG. 23 is a cross-section of an example of the electrode assembly having a central lumen and lumens to receive conductive wires.

DESCRIPTION OF EMBODIMENTS

Aspects of the present disclosure are generally directed to an electrode assembly for an active implantable medical device (AIMD). An AIMD may include an implantable electronics module and a tissue interface. The electrode assembly that, at least in part, forms the tissue interface.

The electrode assembly may be used with one type of AIMD, a neuro stimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present disclosure may be implemented in any brain stimulator (deep brain stimulators, cortical stimulators, etc.), spinal cord stimulator or other neuro stimulator now known or later developed, such as cardiac pacemakers/defibrillators, functional electrical stimulators (FES), pain stimulators, etc. Embodiments of the present disclosure may also be implemented in AIMDs that are implanted for a relatively short period of time to address acute conditions, as well in AIMDs that are implanted for a relatively long period of time to address chronic conditions.

The electrode assembly in accordance with embodiments of the present disclosure are not limited to devices that deliver electrical stimulation signals to a patient. For instance, in certain embodiments, the electrode assembly may be used to receive, record or monitor the physiological response of a patient's tissue to, for example, a therapy. In such embodiments, the electrodes receive a signal from the patient's tissue representing the physiological response. An electrode assembly of the present disclosure that delivers electrical stimulation signals to, or receives signals from, a patient's tissue may also include one or more other components, such as therapeutic agent delivery systems, sensors, etc., that interface with the patient's tissue.

Figure 1:
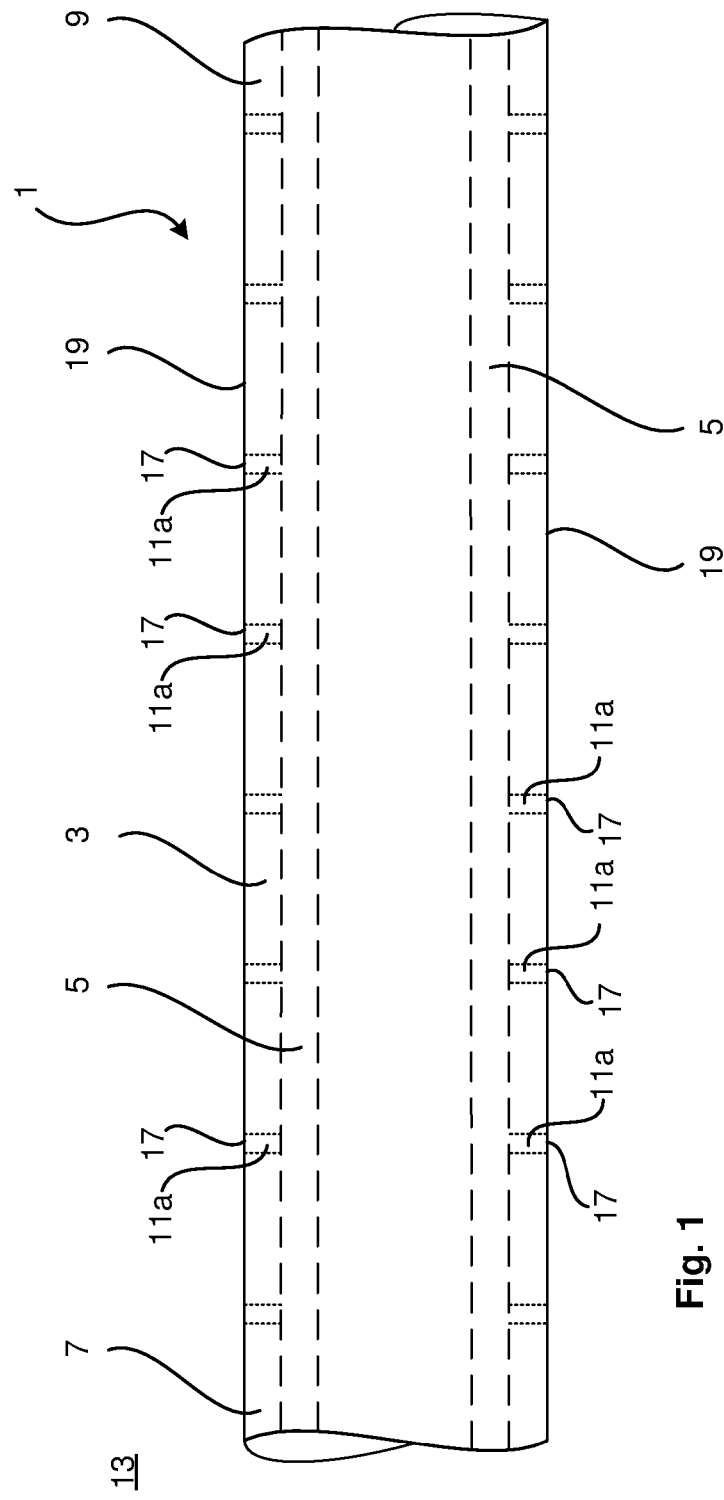
FIG. 1 illustrates an electrode assembly for an active implantable medical device having a plurality of apertures.
Figure 2:
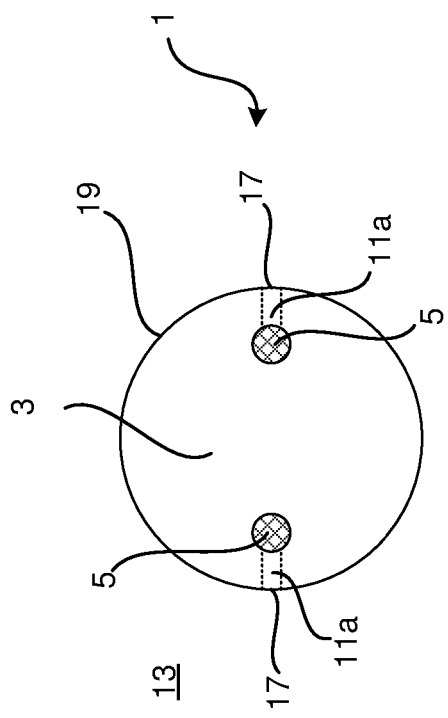
FIG. 2 is a cross-section of the electrode assembly of FIG. 1.

The present disclosure relates to an electrode assembly 1 for an active implantable medical device and a method 100 for manufacturing the electrode assembly 1. Referring to FIGS. 1 and 2, the electrode assembly 1 includes an elongated, biocompatible, electrically non-conductive body 3 having a first portion 7 and a second portion 9 (which in this example are proximal to respective opposite first and second ends). One or more biocompatible, electrically conductive filaments 5 are inside the non-conductive body 3 between the first portion 7 and the second portion 9. The electrode assembly 1 may further include one or more fluid passages 11 along the elongated electrically non-conductive body between the first portion 7 and the second portion 9, wherein the one or more fluid passages 11 allow a surrounding fluid 13 of a patient to be in electrical contact with the one or more conductive filaments 5.

The fluid passages 11 allow the surrounding fluid in the patient, which may include a saline solution (i.e. ionic solution that is at least partially electrically conductive) to provide additional electrical paths. As described above, it is noted that an MRI generates three types of fields that can cause heating of in conventional electrodes. This may include RF frequencies that induce an alternating current at the surface of wire filaments of the electrode. This alternating current may be sufficiently high so as to heat the wire and so any means to reduce the current flow in the wire reduces the heating. In a conventional lead design the wires are imbedded in an insulator. The wire itself is capacitively coupled to the ionic solution in which it resides. The current would flow from the wire to solution and back to the wire thus reducing the current flow in the wire and reducing the heating. By providing an additional electrical path (via the surrounding fluid) this reduces (or eliminates) the induced current due to exposure of the electromagnetic fields in the MRI environment. Any step which increases the capacitance to the fluid reduces the resistance for the current to flow into the solution and hence reduces the heating effect. Increasing the capacitance will reduce resistivity to the solution and further reduce the heating effect. One form is to have the insulator as thin as possible to have the highest capacitance as possible and reduce the resistance to the solution. Unfortunately this may be in conflict with the other goal that needs to be met by implanted leads, such as having a lead that is robust inside the body. This goal necessitates the addition of insulating materials (for support). One way to overcome the competing aims is to provide polymeric support that is porous such that fluid can completely surround the wire. The wires may be insulated with thin insulation such as vapour deposited polymers (such a polymers known as PARYLENE) as a coating or Teflon coating.

Effectively increasing the capacitance with respect to the solution in this manner may not affect the conduction of the lower frequency pulse trains used for stimulation (such as when used with the AIMD), as these will take the lower resistance path such as the core of the electrically conductive filaments 5. This allows examples of the electrode assembly 1 to function as intended whilst being safe when exposed to an MRI.

Furthermore, the elongated electrically non-conductive body 3 may function to provide structural support to the conductive filaments 5 which may be thin wire(s). This is in contrast to using bare wire filaments as electrode assemblies.

In some examples the capacitance of the electrode assembly 1 is in the range of 0.25 nanofarads to 3.30 nanofarads per metre. This may include designing the electrode assembly 1 to have a capacitance in this range when surrounded with the surrounding fluid 13 and/or when coupled with the active implantable medical device. In another example, the specified capacitance range may be between 0.5 nanofarads to 1 nanofarads per metre. In further examples, the capacitance range may be between 1 nanofarads and 3 nanofarads per metre. In yet further examples, the specified capacitance range may be between 1.5 nanofarads and 2.5 nanofarads per metre. Achieving the desired capacitance range may include configuring the electrode assembly with combinations of one or more of: the thickness of the elongated, biocompatible, electrically non-conductive body 3; selection of material for the non-conductive body 3; forming fluid passages 11 along the non-conductive body to the conductive filaments; the size, number and location of the fluid passages 11; porosity of the porous support body 43, 73; the size, number and dimensions of the electrically conductive filaments 5; and selection of material for the electrically conductive filaments 5.

There is also described a method 100 of manufacturing an electrode assembly 1 for an implantable medical device. This includes manufacturing the electrode assembly 1 to include an elongated biocompatible non-conductive body 3 and locating one or more biocompatible electrically conductive filaments 5 inside the non-conductive body 3. The method also includes forming one or more fluid passages 11 in the non-conductive body 3 so that the surrounding fluid in the patient may be in electrical contact with the one or more conductive filaments when implanted for the reasons described above.

Various examples of the electrode assembly 1 will now be described in detail. In these examples, the elongated length portions and cross-section of the electrode assembly 1 are described. It is to be appreciated that the therapeutic ends and connector ends of these example electrode assemblies 1 may be similar to those described above.

EXAMPLE 1

FIGS. 1 and 2 illustrate an example of the electrode assembly 1. In this example the elongated biocompatible, electrically non-conductive body 3 has a plurality of apertures 17 along the length between the first portion 7 and the second portion 9. The plurality of apertures 17 provide the fluid passages 11a from an outer surface 19 of the electrically non-conductive body 3 to the one or more conductive filaments 5 therein. Therefore when implanted, the surrounding fluid 13 may flow into the fluid passages 11a and be in electrical contact with the filaments 5.

Referring to the cross-section in FIG. 2, the fluid passages 11a may extend radially outward from the conductive filaments 5 inside the non-conductive body 3.

The elongated biocompatible electrically non-conductive body 3 may comprise of a biocompatible non-biodegradable polymer. Examples of such polymers may include thermoplastic polyurethanes (such as those under the trade name PELLETHANE offered by Lubrizol Corporation) and silicon rubbers.

The biocompatible, electrically conductive filaments 5 may include a metal or metallic alloy. An example of such conductive filaments 5 may include platinum, platinum iridium alloys, MP35N stainless steel. In some examples, the electrically conductive filaments 5, as noted above, may have a thin insulation such as a vapour deposited polymer coating or Teflon coating.

Figure 3:
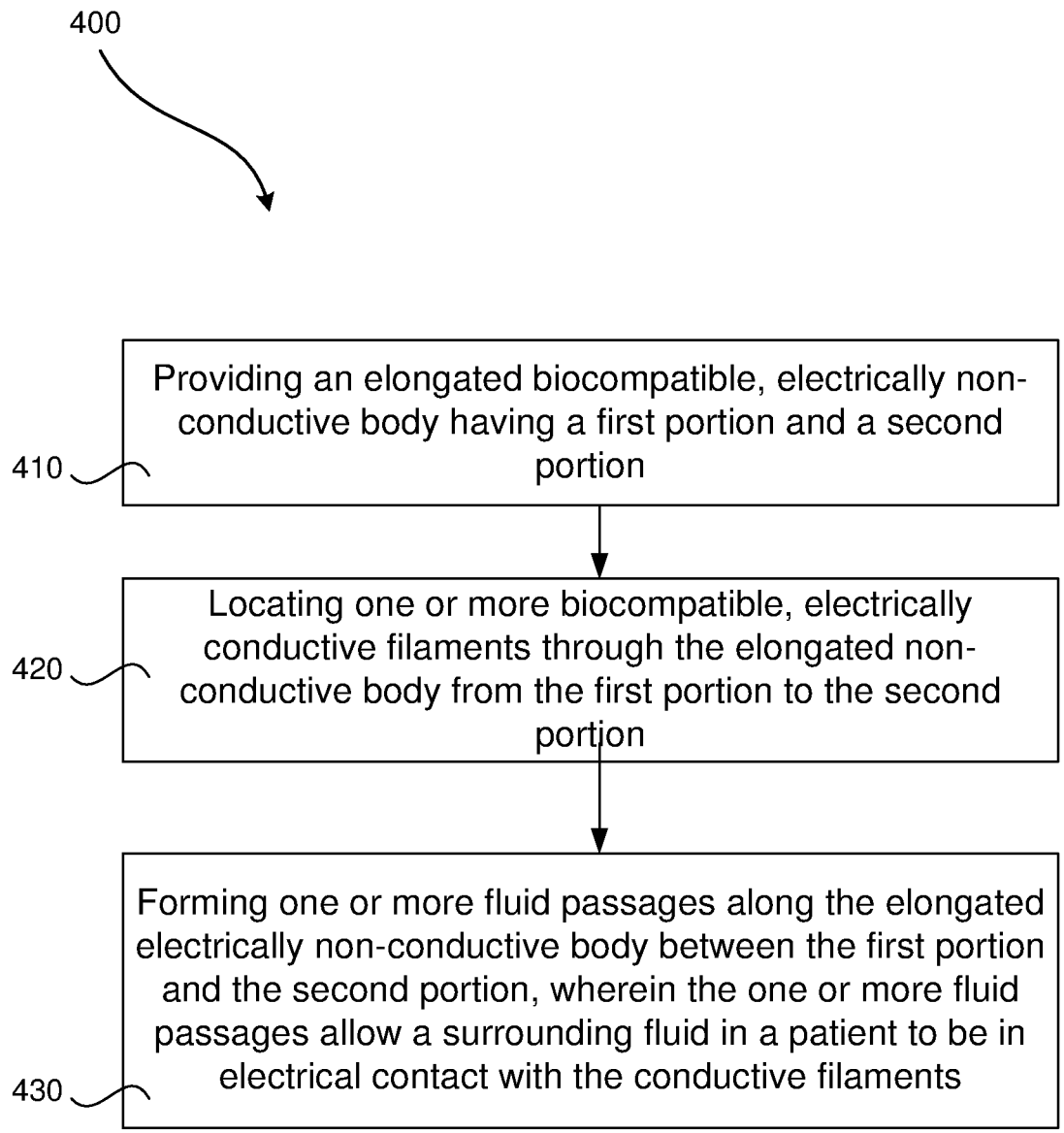
FIG. 3 is a flow diagram of a method to manufacture an electrode assembly.

A method 400 of manufacturing the electrode assembly 1 is shown in the flow diagram in FIG. 3. This includes providing 410 the elongated biocompatible, electrically non-conductive body 3 having a first portion 7 and a second portion 9. In some examples, the electrically non-conductive body may be extruded through a die.

The method 400 also includes locating one or more biocompatible, electrically conductive filaments 5 inside the elongated non-conductive body 3. This may include inserting the conductive filaments 5 through lumens in the electrically non-conductive body 3. In other examples, this may include feeding the conductive filaments 5 through an extruder as the electrically non-conductive body 3 is formed.

The method also includes forming one or more fluid passages 11 along the electrically non-conductive body 3 so that when the electrode assembly 1 is implanted, the surrounding fluid 13 in a patient is in electrical contact with the conductive filaments 5. In some examples, the fluid passages 11 are formed by laser cutting the non-conductive body 3. In other examples, the fluid passages 11 are formed during extrusion of the non-conductive body 3, where the die creates the fluid passages 11.

It is to be appreciated that examples of the method 400 may have steps performed in different orders than that shown in FIG. 3.

EXAMPLE 2

Figure 4:
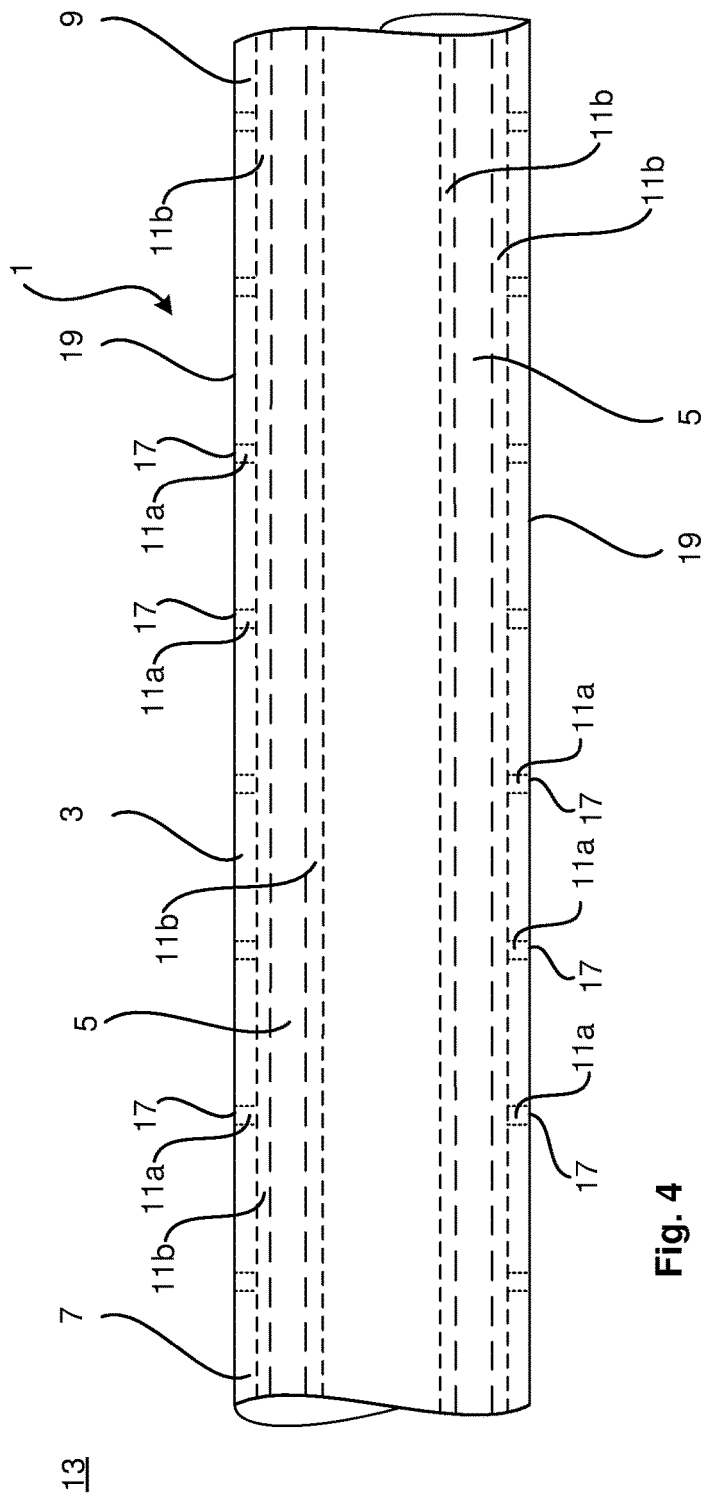
FIG. 4 illustrate another example of an electrode assembly for an active implantable medical device having a conductive filament lumen with a greater diameter than the conductive filament.
Figure 5:
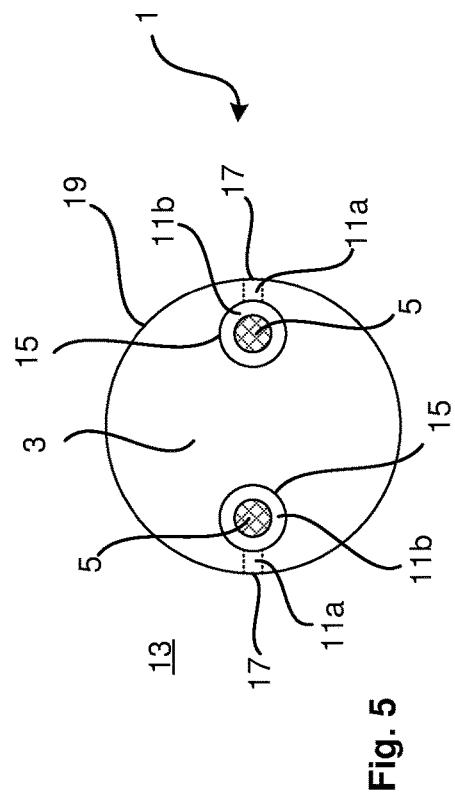
FIG. 5 is a cross-section of the electrode assembly of FIG. 4.

FIGS. 4 and 5 illustrate another example of the electrode assembly 1. In this example the electrode assembly 1 may be the main lead of a percutaneous lead. Accordingly, the electrode assembly 1 may incorporate features of known percutaneous leads with the exception of the features discussed below.

The elongated non-conductive body 3 may include one or more conductive filament lumens 15 that extend lengthwise inside the elongated body. These conductive filament lumens 15 may receive respective conductive filaments 5. The conductive filament lumens 15 may have a greater diameter than the conductive filaments 5 so that there is space between the walls of the conductive filament lumens 15 and the conductive filaments 5 for fluid to permeate through. That is, the conductive filament lumens 15 would be larger than conventionally provided for a given filament 5 size. Thus the conductive filament lumens 15 provide at least part of the one or more fluid passages 11b for the surrounding fluid to be in electrical contact with the filament.

Referring to FIGS. 4 the one or more fluid passages may also include additional fluid passages 11a that fluidly connects the conductive filament lumens 15 towards the outer surface 19 and the surrounding fluid 13. These additional fluid passages 11a may be provided along the length of the elongated non-conductive body 3.

It is to be appreciated that the lumens 15 may be formed by providing a corresponding shape to the die during extrusion.

EXAMPLE 3

Figure 6:
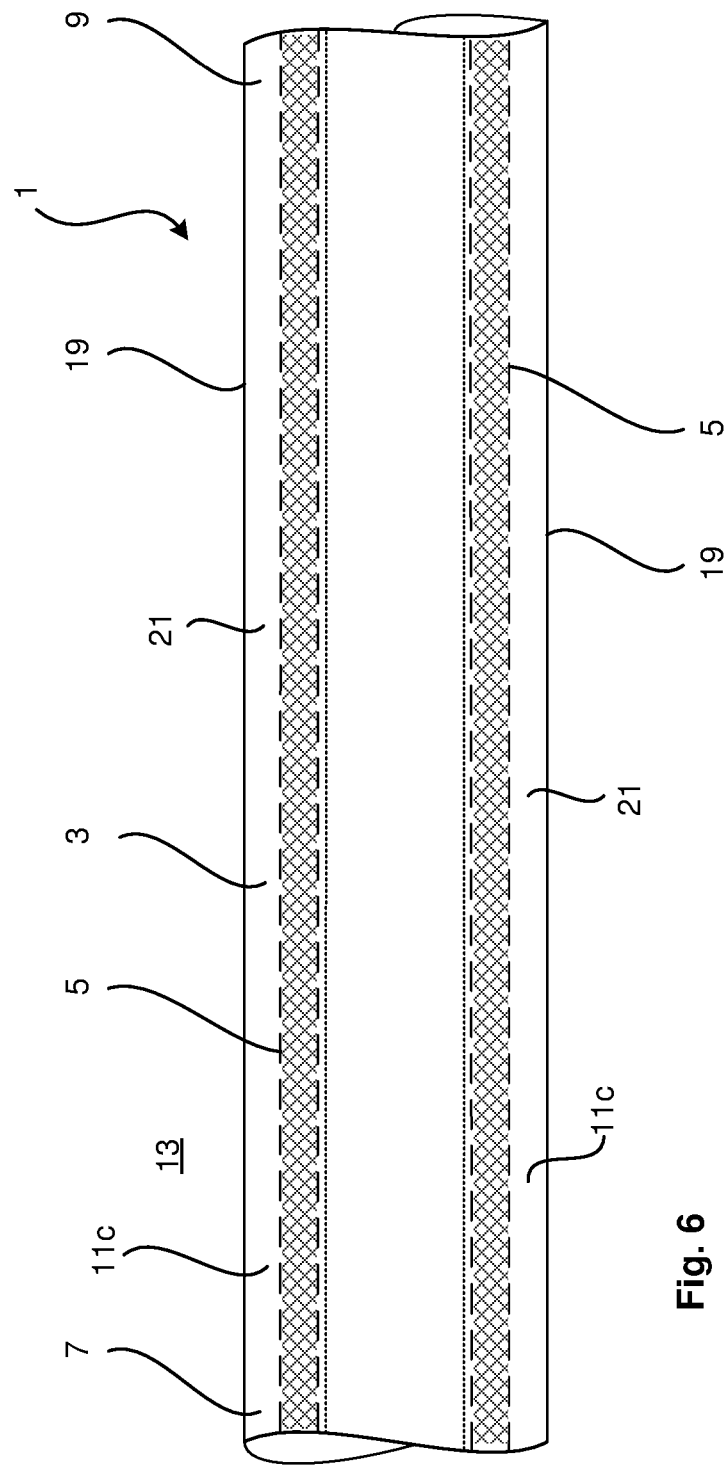
FIG. 6 illustrates yet another example of an electrode assembly for an active implantable medical device having channels.
Figure 7:
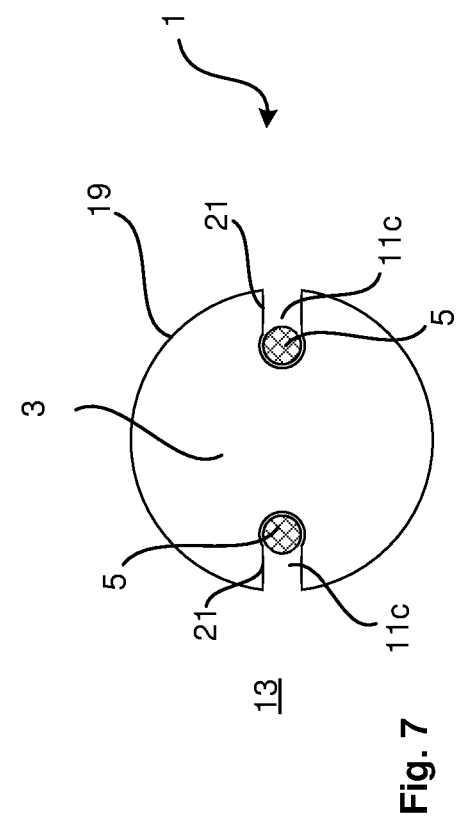
FIG. 7 is a cross-section of the electrode assembly of FIG. 6.

FIGS. 6 and 7 illustrate another example of the electrode assembly 1. In this example, one or more channels 21 may be provided along the elongated electrically non-conductive body 3. The one or more channels 21 provides the one or more fluid passages 11c from an outer surface 19 of the non-conductive body 3 to the one or more conductive filaments 5.

In some examples, the filaments 5 may be inserted into the channels 21 and held in place therein. For example, the channels 21 may include widened bottom and a narrower mouth such that a filament 5 may be pressed into place at the widened bottom. The resilience of the non-conductive body 3 may provide compression force or otherwise hold the filament 5 in place.

It is to be appreciated that these channels 21 may be formed by having a die with a corresponding shape to form channels 21 during extrusion of the non-conductive body 3.

EXAMPLE 4

In the examples described herein, the one or more fluid passages 11 may be provided with respective one or more plugs 23. Referring to FIG. 8, a plug 23 made of a biocompatible biodegradable material is provided in the fluid passages 11 so that the fluid passages 11 are plugged during implantation into a patient. This may assist implantation as open fluid passages 11 may cause catch points or otherwise impede insertion. This may also assist by allowing existing implantation devices, surgical tools and techniques to be used.

After implantation, the plugs 23 may biodegrade in the body of the patient thereby allowing the surrounding fluid to flow into the fluid passages 11.

The biocompatible biodegradable material may include polyvinyl alcohol (PVA), polylactic acid (PLA), polyglycolic acid (PGA), and poly(lactic-co-glycolic) acid (PLGA).

Thus in some examples of manufacturing the electrode assembly 1, the method 400 may include filling the one or more fluid passages 11 with the one or more plugs 23.

EXAMPLE 5

FIG. 9 illustrates another example of the electrode assembly 1 that further includes a biocompatible biodegradable material to cover the fluid passages 11. In this example, a biocompatible biodegradable sheath 25 is provided to surround the elongated non-conductive body 3. This sheath may be a tube-like sheath provided around the outer surface (19) of the non-conductive body 3. The biodegradable sheath 25 may provide a smooth outer surface to assist in implantation of the electrode assembly 1. The sheath 25 (as well as plugs 23 described above) may also function to protect the fluid passages 11 from contamination until they have been implanted. For example, preventing dust, other foreign objects, blood, etc. from entering into the fluid passages 11 and preventing the surrounding fluid 13 flowing into the fluid passages 11.

Once the electrode assembly 1 is implanted, the biodegradable sheath 25 may then biodegrade into the body of the patient and allow the fluid passages 11 to operate as discussed herein.

It is to be appreciated that the biodegradable plugs 23 and biodegradable sheaths 25 in examples 4 and 5 may be used with other electrode assemblies described in the other examples.

Thus in some examples of manufacturing the electrode assembly 1, this includes surrounding the non-conductive body 5 with the biodegradable sheath 25. In some examples, this may include dipping or spraying the non-conductive body 5 with the biodegradable material. In other examples, the may include sliding the sheath 25, in the form of a tube, over the non-conductive body 5.

EXAMPLE 6

Figure 10:
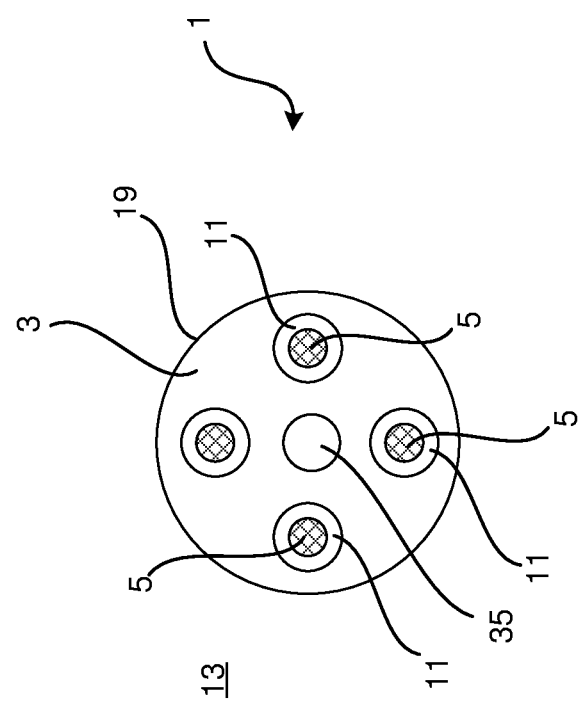
FIG. 10 illustrates a cross-section of an example of an electrode assembly having a central lumen to receive a stylet.

FIG. 10 illustrates an example of an electrode assembly 1 further comprising a central lumen 35 in the elongated electrically non-conductive body 3. The central lumen 35 may receive a stylet to assist implantation. It is to be appreciated that a central lumen 35 may be applied to some of the other examples of the electrode assembly described herein.

EXAMPLE 7

Figure 11:
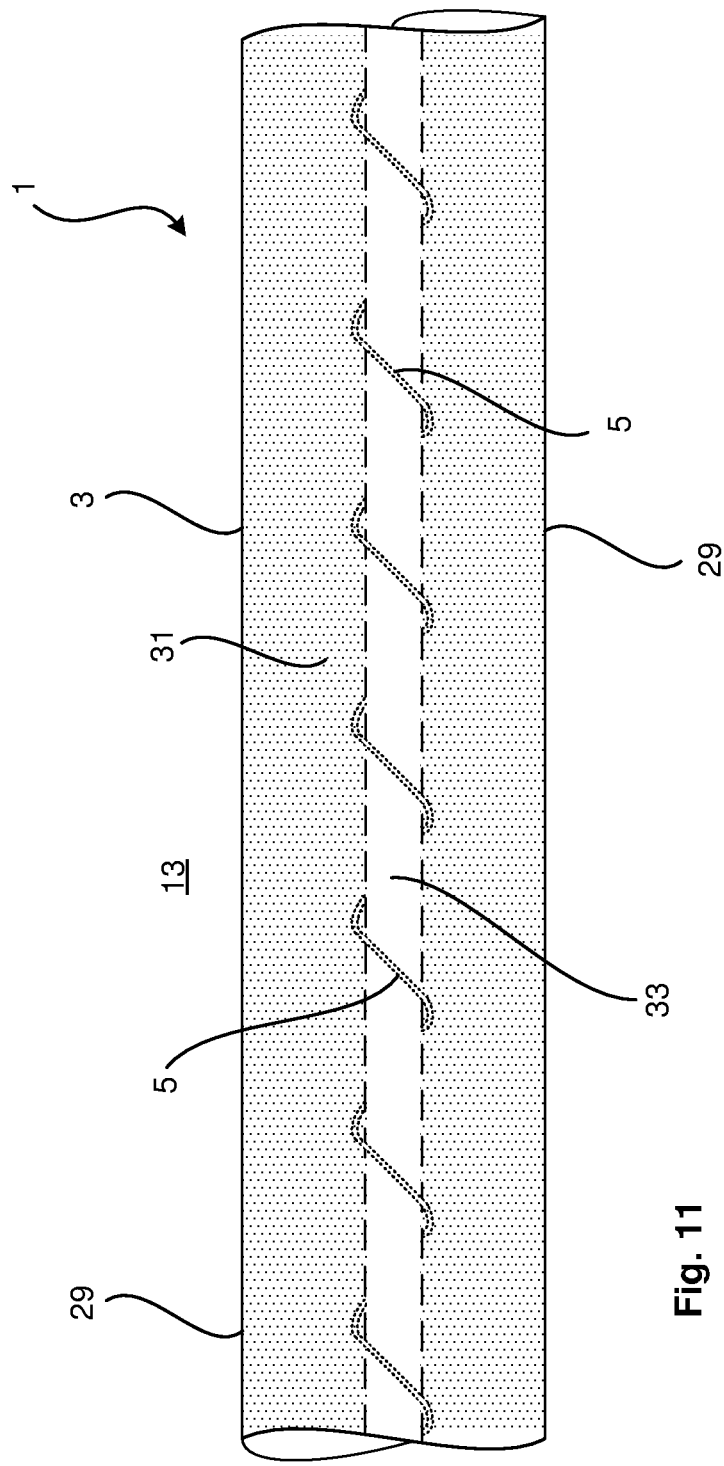
FIG. 11 illustrates another example of an electrode assembly for an active implantable medical device having an outer wall and biodegradable material within.
Figure 12A:
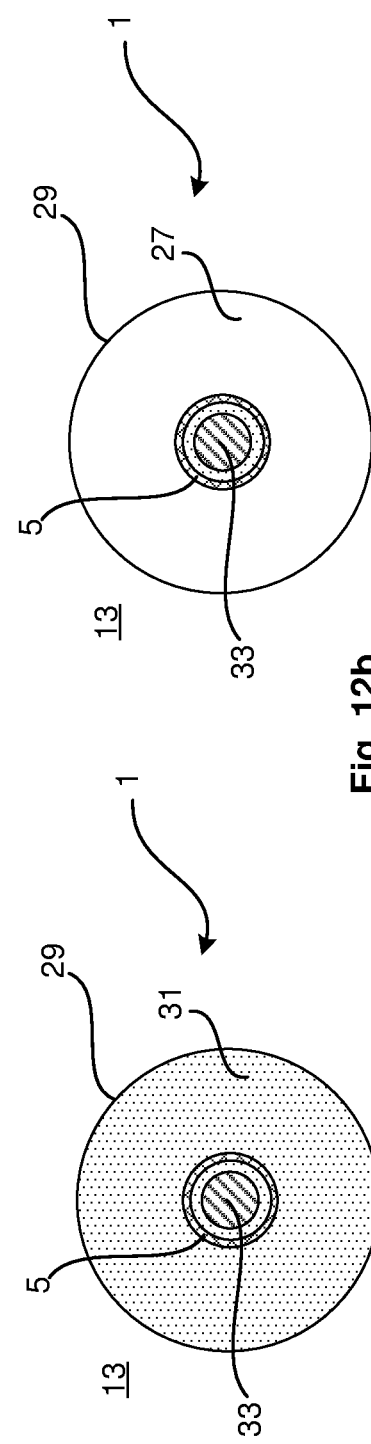
FIG. 12a is a cross-section of the electrode assembly of FIG. 11 with the biodegradable material.
Figure 12B:
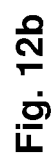
FIG. 12b is a cross-section of the electrode assembly of FIG. 11 without the biodegradable material after implantation.

FIGS. 11, 12a and 12b illustrate another example of the electrode assembly 1, wherein the elongated non-conductive body 3 comprises an outer wall 29 that defines a cavity 27 within the outer wall 29. The cavity 27 contains the one or more conductive filaments 5 along the elongated cavity 27. In one example, the conductive filaments 5 are surrounded with a biodegradable material 31 that is also inside the cavity 27 as shown in FIG. 12a.

After implantation, the biodegradable material 31 biodegrades into the body of the patient, and the cavity 27 then forms at least part of the one or more fluid passages 11d to allow surrounding fluid 13 to be in electrical contact with the filaments as shown in FIG. 12b. It is to be appreciated that additional apertures could be provided in the outer wall 29 or elsewhere (such as end portions) of the non-conductive body 3 to provide further fluid passages 11.

Furthermore, as illustrated in FIGS. 11, 12a and 12b, the electrode assembly 1 may also include a core 33 disposed in the cavity 27. The one or more conductive filaments 5 may be helically disposed around the core 33. The core 33 is preferably made of a biocompatible and non-biodegradable material.

In one variation (not shown), the core 33 of the electrode assembly may further include a central lumen 35 to receive a stylet to aid implantation.

EXAMPLE 8

Figure 13:
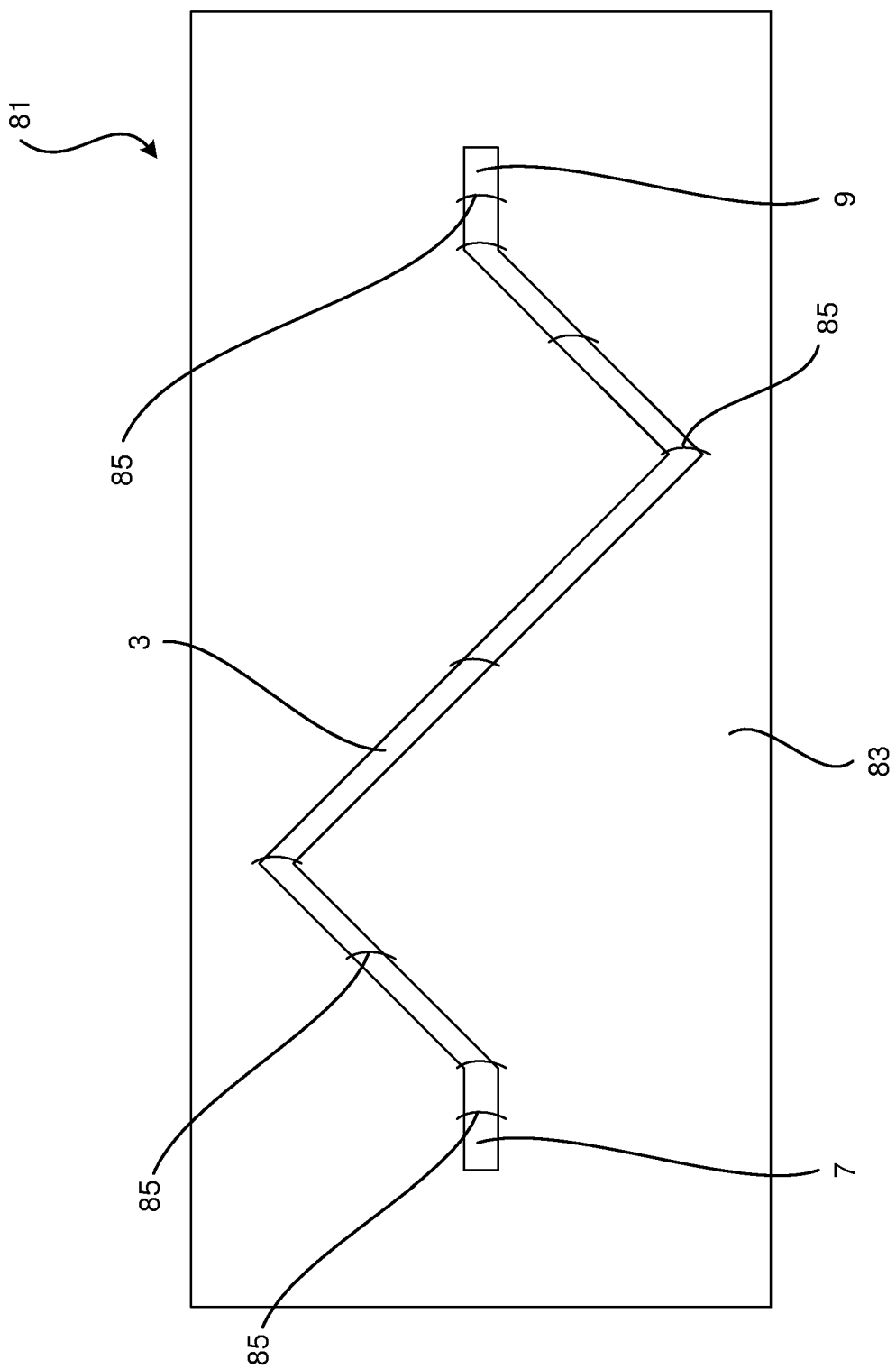
FIG. 13 illustrates another example of an electrode assembly that includes a non-conductive body, having the conductive filaments passing through, stitched to a non-conductive base.

FIG. 13 illustrates another example of an electrode assembly 81. In this example, the electrode assembly further comprises a biocompatible, electrically non-conductive needle-piercable base 83. The elongated electrically non-conductive body 3, that has the one or more conductive filaments 5 passing inside, is stitched to the electrically non-conductive needle-piercable base 83. The electrically non-conductive body 3, and the conductive filaments 5, may configured as described in the other examples of the electrode assembly 81 described herein. As used herein, stitching a conductive filament to a base refers to sewing, embroidering or otherwise securing the filament to the base through the use of hand or machine needlework.

The electrically non-conductive needle piercable base 83 may provide additional support and structure to the electrode assembly 81. This may assist in implantation and/or retention of the electrode assembly 81 in the patient.

The non-conductive needle-piercable base 83 may comprise, for example, woven or continuous fabric, a solid sheet or film of synthetic material, etc. In some examples, the non-conductive needle-piercable base 83 is a solid sheet or film of thermoplastic material. In such examples, a heated needle is used to stitch a thread to secure the electrically non-conductive body 3 to the needle-piercable base 83 sot that the material around each perforation will melt and re-seal after the stitch is formed. The re-sealing of the needle-piercable base 83 secures the thread to the base 83 thereby increasing reliability. In some examples, having a thermoplastic base 83 may be advantageously as it can be molded into a desired shape before or after stitching with the thread.

The stitch may be formed with a thread, such as a biocompatible, electrically non-conductive filament 85 sewn into the base 83. However depending on application, the thread may include an electrically conductive filament to conduct electrical current.

EXAMPLE 9

Figure 14:
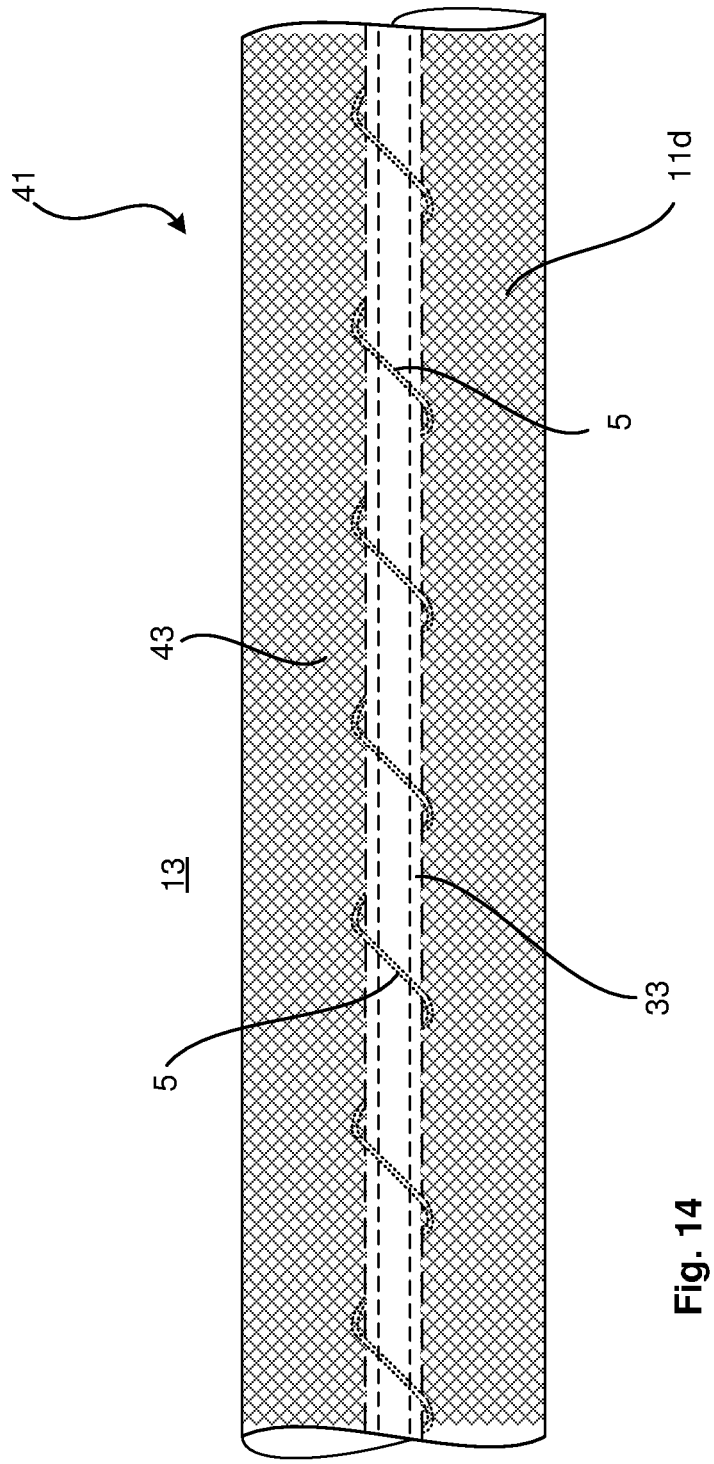
FIG. 14 illustrates another example of an electrode assembly for an active implantable medical device that includes a porous support body.
Figure 15:
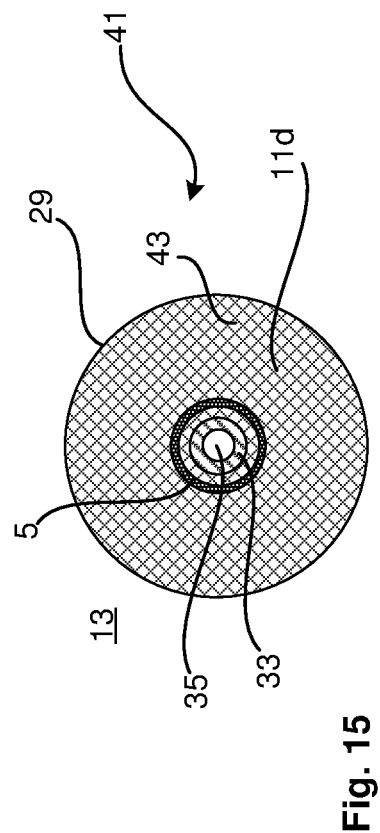
FIG. 15 is a cross-section of the electrode assembly of FIG. 14.

FIGS. 14 and 15 illustrate yet another example of an electrode assembly 41. In this example, the electrode assembly 41 comprises a biocompatible porous support body 43. One or more biocompatible electrically conductive filaments 5 are provided to inside the porous support body 43 from a first portion 7 to a second portion 9. The porous support body 43 provides fluid passages 11*d* through the pores to allow the surrounding fluid 13 in a patient to be in electrical contact with the one or more electrically conductive filaments 5.

Examples of porous material include porous films of ultra-high molecular weight polyethylene (HDPE).

Figure 16:
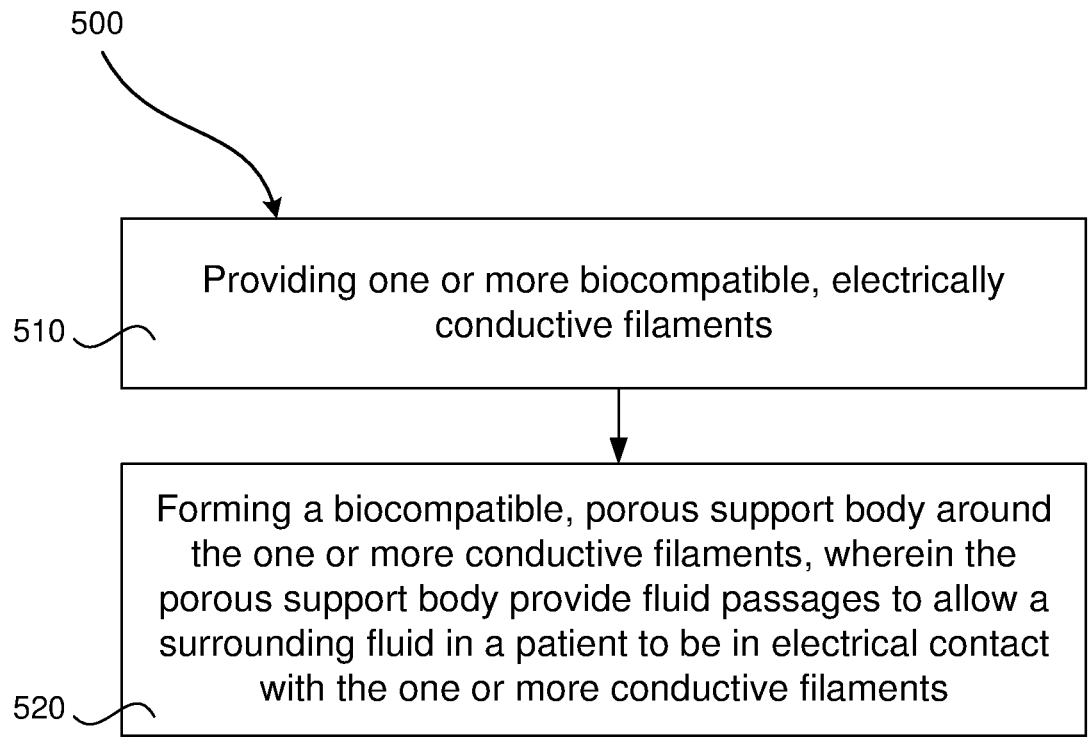
FIG. 16 is another flow diagram of a method to manufacture an electrode assembly.

FIG. 16 illustrates an example of a method 500 of manufacturing the electrode assembly 41 including providing 510 one or more biocompatible, electrically conductive filaments 5; and forming a biocompatible, porous support body 43, 73 around the one or more electrically conductive filaments 5. In some examples, forming the porous support body 43, 73 may include moulding the porous support body 43 with the electrically conductive filaments in the mould. In other examples, this may include dipping or spraying the electrically conductive filaments 5 with a porous material.

In one example, the electrode assembly 41 further comprises a core 33 disposed in the porous support body 43. One or more of the electrically conductive filaments 5 may be helically disposed around the core 33.

In yet a further variation, the core 33 may include a central lumen 35 to receive a stylet.

EXAMPLE 10

Figure 17:
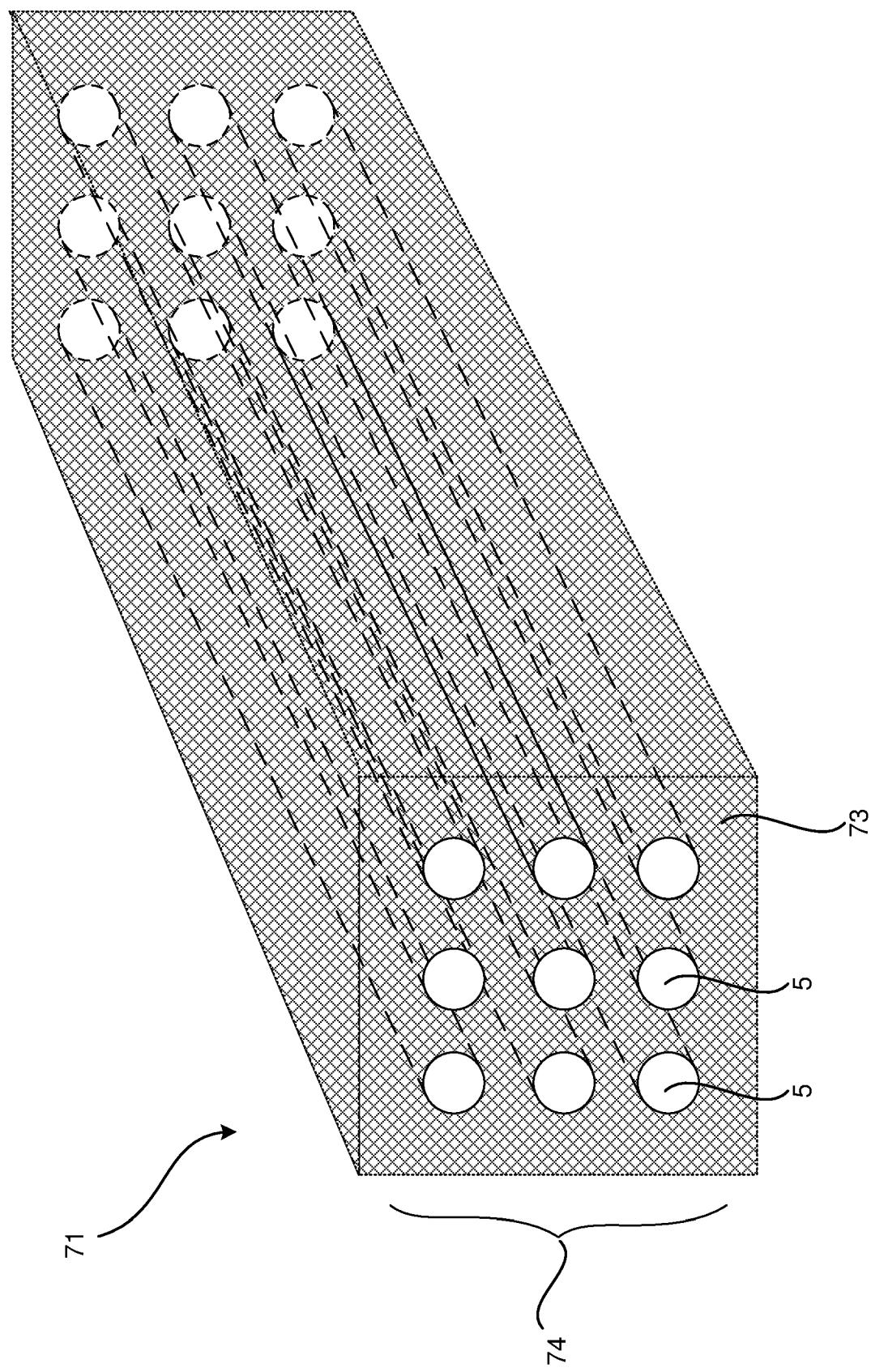
FIG. 17 illustrates another example of an electrode assembly for an active implantable medical device that has a porous support body and a plurality of conductive filaments arranged in a matrix pattern.

FIG. 17 illustrates yet another embodiment of the electrode assembly 71. In this example there is a biocompatible porous support body 73 that has a plurality of biocompatible electrically conductive filaments 5 passing inside. The plurality of conductive filaments 5 are arranged in a matrix 74 in the porous support body 73.

It is to be appreciated that the arrangement of the conductive filaments 5 may include other patterns (when viewed in a cross section).

In some examples, the plurality of conductive filaments 5 are substantially parallel to one another between the first portion 7 and second portion 9 of the porous support body 73. Having the conductive filaments 5 extending parallel to one another may prevent, or reduce the likelihood, of the conductive filaments 5 from directly contacting one another. For example, if the electrode assembly 71 is twisted or bent.

EXAMPLE 11

Figure 19:
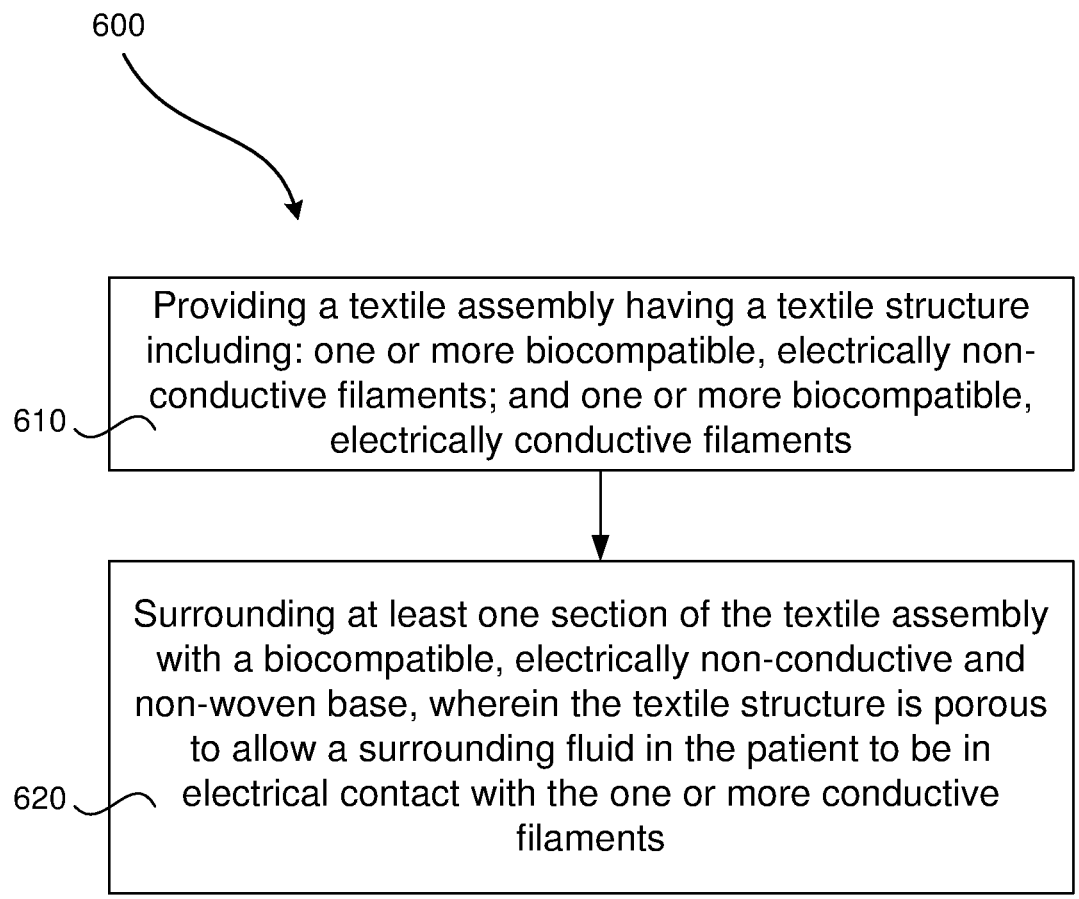
FIG. 19 is yet another flow diagram of a method to manufacture an electrode assembly.

FIGS. 18*a* and 18*b* illustrate another example of an electrode assembly 51 for an AIMD. The electrode assembly 51 is manufactured by a method shown in FIG. 19 that includes providing 610 a textile assembly 53 having a textile structure 55 and surrounding 620 at least a section of the textile assembly 53 with a bio-compatible, electrically non-conductive and non-woven base 59

The textile assembly 53 comprises one or more biocompatible electrically non-conductive filaments 57 and one or more biocompatible, electrically conductive filaments 5. The textile structure 55 is porous to allow a surrounding fluid 14 in a patient to pass into the pores and be in electrical contact with the one or more conductive filaments 5. It is to be appreciated that additional passages and aperture may be provided to allow the surrounding fluid a passage from outside the electrode assembly 51 to the textile structure 57.

Exemplary textile manufacturing methods include, but are not limited to, weaving, knitting, braiding, crocheting, etc. For ease of illustration, the examples below will be primarily discussed herein with reference to knitting or braiding. It would be appreciated that other textile manufacturing methods are also within the scope of the present disclosure.

In some examples, the textile assembly 53 is a knitted assembly 53 and the textile structure 55 is an intermeshed loop structure 55 as illustrated in FIG. 18*a*. In some examples, the one or more biocompatible, electrically non-conductive filaments 57 are arranged in substantially parallel rows each stitched to an adjacent row with one or more loops. The one or more biocompatible, electrically conductive filaments 5 are intertwined with the one or more row of non-conductive filaments 57. The intermeshed loop structure 55 may also include a central lumen 303 to receive a stylet.

FIG. 18*b* illustrates the electrode assembly 51 with the knitted assembly surrounded by the non-conductive and non-woven base 59.

EXAMPLE 12

Figure 20A:
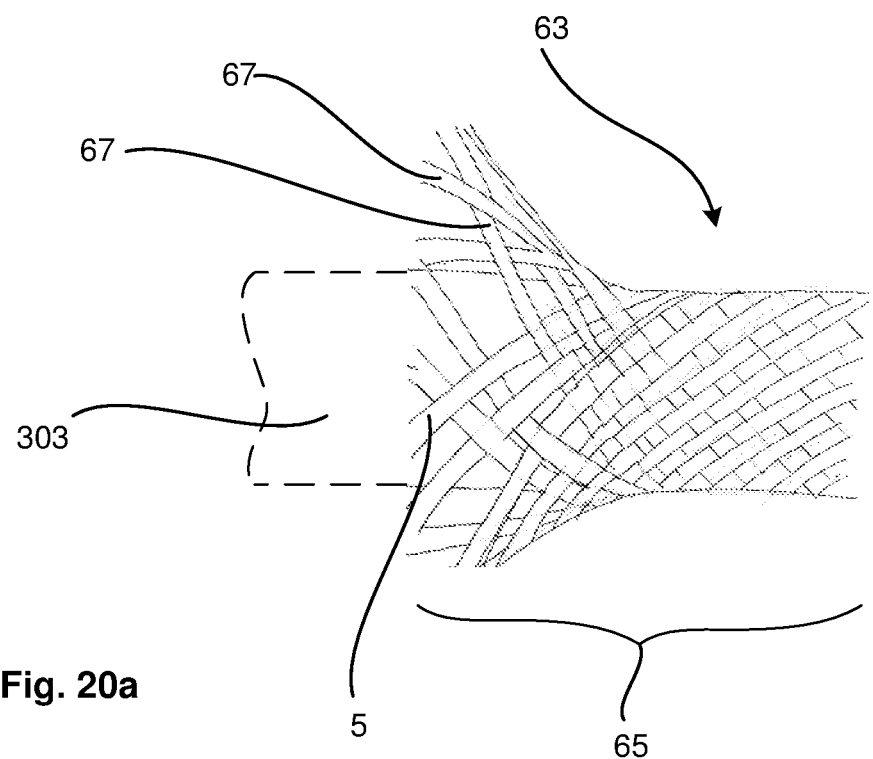
FIGS. 20a and 20b illustrates another example of an electrode assembly for an active implantable medical device having a braided assembly.
Figure 20B:
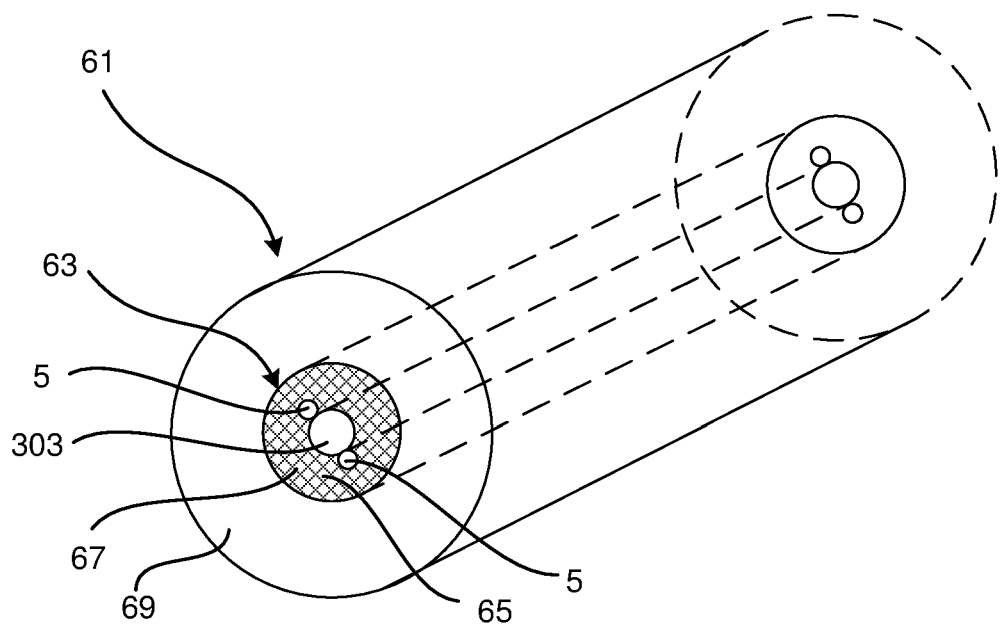

FIGS. 20*a* and 20*b* illustrate another example of an electrode assembly 61 with a textile assembly 63 comprising of a textile structure 65 that is braided. Referring to FIG. 20*a*, the braided structure 65 comprises braiding of the one or more non-conductive filaments 67 and the one or more conductive filaments 5. The textile structure 65 may have a central lumen 303 to allow a stylet to pass through. FIG. 20*b* illustrates the electrode assembly 61 with the braided structure 65, as shown in FIG. 20*a*, that is surrounded by the non-conductive and non-woven base 69.

EXAMPLE 13

Figure 21:
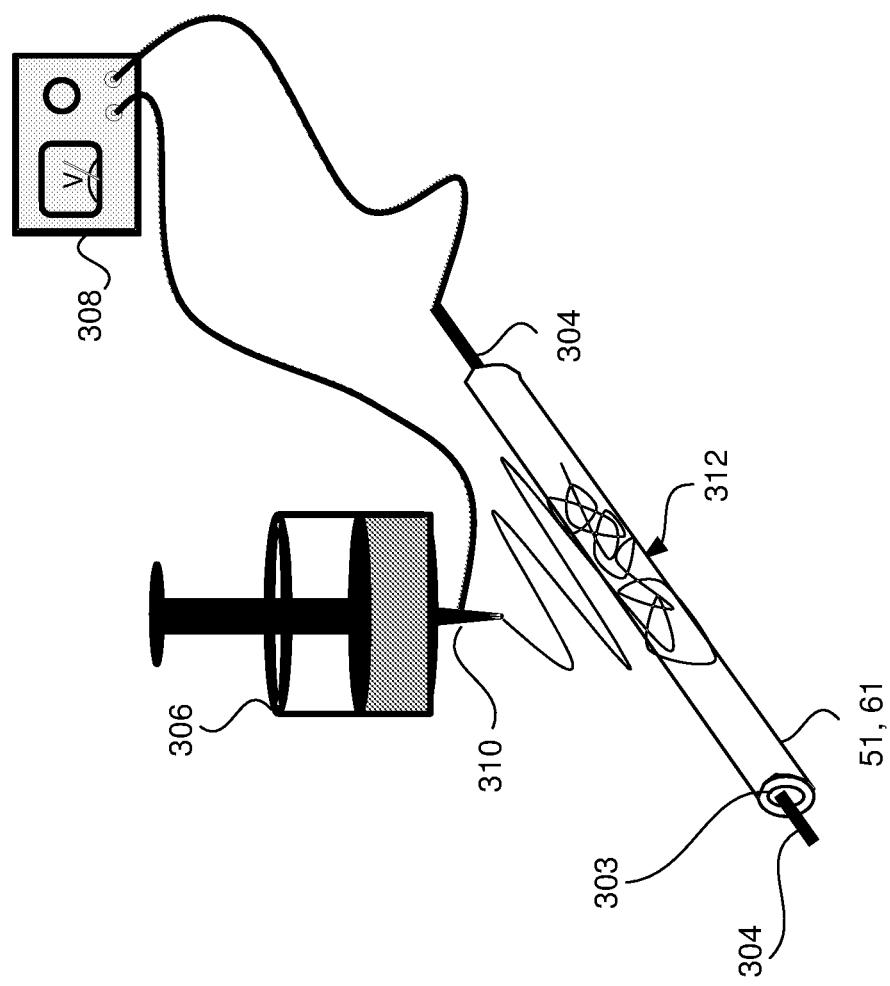
FIG. 21 illustrates an example of electrospinning a material to the electrode assembly.

In some examples, the bio-compatible, electrically non-conductive and non-woven base 59, 69 is applied to surround a section of the textile assembly 53, 63 by electrospinning. FIG. 21 illustrates how an electrospinning process may be applied to create a cover (the non-conductive and non-woven base 59, 69) of an electrode assembly 51, 61. The electrode assembly 51, 61 includes an electrically non-conductive support member and electrically conductive filaments for stimulation. A conductive stylet 304 is inserted in a lumen 303 in of the electrode assembly 51, 61. Then, a suitable polymer material, such as PET, is loaded into a syringe delivery system 306. A high voltage source 308 is connected to the syringe nozzle 310 and the conductive stylet 304. The non-woven coating 312 is formed around the electrode assembly 51, 61 by suitably moving the lead / stylet assembly 302/304 beneath the syringe. As a result, the electrode assembly 51, 61 is provided with a cover made of an electrically non-conductive and non-woven base 59, 69. The base 59, 69 may include openings between the strand that is formed by the electrospinning process, which may in turn provide the one or more fluid passages 11 for the surrounding fluid in a patient to be in electrical contact with the conductive filaments 5. The movement of the lead/stylet assembly 302/304 beneath the syringe is such that the openings formed by the strand are dimensioned such that the openings allow stimulation of tissue by the electrodes while preventing tissue ingrowth.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An electrode assembly for an active implantable medical device comprising:
   an elongated, biocompatible, electrically non-conductive body having a first portion and a second portion;
   one or more biocompatible, electrically conductive filaments inside the elongated non-conductive body between the first portion and the second portion, the one or more conductive filaments being electrically insulated;
   one or more fluid passages along the elongated electrically non-conductive body between the first portion and second portion, the one or more fluid passages allowing a surrounding fluid of a patient to be in electrical contact with the one or more conductive filaments; and
   one or more channels along the elongated electrically non-conductive body, the one or more channels providing the one or more fluid passages from an outer surface of the electrically non-conductive body to the one or more conductive filaments.

2. The electrode assembly according to claim 1 comprising:
   a plurality of apertures along the elongated electrically non-conductive body, the plurality of apertures providing the fluid passages from the outer surface of the electrically non-conductive body to the one or more conductive filaments.

3. The electrode assembly according to claim 1 comprising:
   one or more conductive filament lumens to receive respective conductive filaments passing through the elongated electrically non-conductive body, the one or more conductive filament lumens having a diameter greater than the respective conductive filament to provide at least part of the one or more fluid passages.

4. The electrode assembly according to claim 1 comprising:
   one or more plugs in the one or more fluid passages, the plugs comprising a biocompatible biodegradable material for biodegrading in a body of the patient after implantation.

5. The electrode assembly according to claim 1 further comprising:
   a biocompatible biodegradable sheath to surround the elongated electrically non-conductive body, the biodegradable sheath biodegrading in a body of the patient after implantation.

6. The electrode assembly according to claim 1 further comprising a central lumen in the elongated electrically non-conductive body to receive a stylet.

7. The electrode assembly according to claim 1, wherein the biocompatible, elongated electrically non-conductive body comprises:
   an outer wall; and
   a cavity within the outer wall, the cavity containing the one or more conductive filaments disposed within a biocompatible biodegradable material,
   the biodegradable material biodegrading in a body of a patient after implantation.

8. The electrode assembly according to claim 7, further comprising a core disposed in the cavity, the one or more filaments being helically disposed around the core.

9. The electrode assembly according to claim 1 further comprising:
   a biocompatible, electrically non-conductive and needle-piercable base;
   the elongated electrically non-conductive body, with the one or more conductive filaments, being stitched to the needle-piercable base.

10. The electrode assembly of claim 1 wherein the insulation is configured so that the electrode assembly coupled with the active implantable medical device when in contact with the surrounding fluid has a capacitance in the range of 0.25 nanofarads to 3.30 nanofarads per metre.

11. The electrode assembly of claim 10, wherein the insulation is a vapour deposited polymer coating or a Teflon coating.

12. A method of manufacturing an electrode assembly for an active implantable medical device, comprising:
   providing an elongated biocompatible, electrically non-conductive body;
   locating one or more biocompatible, electrically conductive filaments though the elongated non-conductive body from a first portion to a second portion;
   forming one or more fluid passages along the elongated electrically non-conductive body between the first portion and the second portion, the one or more fluid passages allowing a surrounding fluid of a patient to be in contact with the one or more conductive filaments; and
   forming one or more channels along the elongated electrically non-conductive body, the one or more channels providing the one or more fluid passages from an outer surface of the electrically non-conductive body to the one or more conductive filaments.

13. The method of manufacturing an electrode assembly according to claim 12 further comprising:
   forming a plurality of apertures along the elongated electrically non-conductive body to provide the fluid passages from the outer surface of the electrically non-conductive body to the one or more conductive filaments.

14. The method of manufacturing an electrode assembly according to claim 12, further comprising:
   forming one or more conductive filament lumens inside the elongated electrically non-conductive body to receive respective electrically conductive filaments, the one or more conductive filament lumens having a diameter greater than the respective conductive filament lumens forming at least part of the one or more fluid passages.

15. The method of manufacturing an electrode assembly according to claim 12, further comprising:
   filling one or more fluid passages with one or more plugs, the plugs comprising a biocompatible biodegradable material, the one or more plugs biodegrading in a body of the patient after implantation.

16. The method of manufacturing an electrode assembly according to claim 12, further comprising configuring insulation around the electrically conductive filaments such that the electrode assembly when coupled with the active implantable medical device and in contact with the surrounding fluid has a capacitance in the range of 0.25 nanofarads to 3.30 nanofarads per metre.

17. The method of manufacturing an electrode assembly according to claim 16, further comprising insulating the one or more conductive filaments with a vapour deposited polymer coating or a Teflon coating.

18. An electrode assembly for an active implantable medical device comprising:
   an elongated, biocompatible, electrically non-conductive body having a first portion and a second portion;
   one or more biocompatible, electrically conductive filaments inside the elongated non-conductive body between the first portion and the second portion;
   wherein the electrode assembly is configured to be coupled with the active implantable medical device and in contact with the surrounding fluid to have a capacitance in the range of 0.25 nanofarads to 3.30 nanofarads per metre.

* * * * *